US00PP18434P2

(12) United States Plant Patent
Sakazaki

(10) Patent No.: US PP18,434 P2
(45) Date of Patent: Jan. 15, 2008

(54) ***VERBENA* PLANT NAMED 'USBENA6201'**

(50) Latin Name: *Verbena hybrida*
Varietal Denomination: USBENA6201

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 11/520,897

(22) Filed: Sep. 14, 2006

(51) Int. Cl.
*A01H 5/00* (2006.01)

(52) U.S. Cl. ..... Plt./308

(58) Field of Classification Search ..... Plt./308
See application file for complete search history.

*Primary Examiner*—Kent Bell
*Assistant Examiner*—Annette Para
(74) *Attorney, Agent, or Firm*—C. A. Whealy

(57) ABSTRACT

A new and distinct cultivar of *Verbena* plant named 'USBENA6201', characterized by its outwardly to low spreading and relatively compact plant habit; vigorous growth habit; freely branching habit; freely flowering habit; red purple-colored flowers that are held above and beyond the foliage; and tolerance to Powdery Mildew.

1 Drawing Sheet

Botanical designation: *Verbena hybrida.*
Cultivar denomination: 'USBENA6201'.

BACKGROUND OF THE INVENTION

The present invention relates to a new and distinct cultivar of Verbena, botanically known as *Verbena hybrida,* and hereinafter referred to by the name 'USBENA6201'.

The new *Verbena* is a product of a planned breeding program conducted by the Inventor in Hikone, Shiga, Japan. The objective of the breeding program is to create new disease-resistant and high temperature-tolerant *Verbena* cultivars with semi-upright plant habit and attractive flower coloration.

The new *Verbena* originated from a cross-pollination made by the Inventor on Apr. 8, 2001 in Hikone, Shiga, Japan of a proprietary seedling selection of *Verbena hybrida* identified as code number VJL50-2, not patented, as the female, or seed, parent with a proprietary seedling selection of *Verbena hybrida* identified as code number VJL53-3, not patented, as the male, or pollen, parent. The new *Verbena* was discovered and selected by the Inventor as a single flowering plant within the progeny of the stated cross-pollination in a controlled environment in Bonsall, Calif. on Jun. 6, 2002.

Asexual reproduction of the new *Verbena* by terminal cuttings in a controlled environment in Bonsall, Calif. since Jun. 7, 2002 has shown that the unique features of this new *Verbena* are stable and reproduced true to type in successive generations.

SUMMARY OF THE INVENTION

The cultivar USBENA6201 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'USBENA6201'. These characteristics in combination distinguish 'USBENA6201' as a new and distinct cultivar of *Verbena:*

1. Outwardly to low spreading and relatively compact plant habit.
2. Vigorous growth habit.
3. Freely branching habit.
4. Freely flowering habit.
5. Red purple-colored flowers that are held above and beyond the foliage.
6. Tolerant to Powdery Mildew.

Plants of the new *Verbena* can be compared to plants of the female parent selection. Plants of the new *Verbena* differ from plants of the female parent selection in the following characteristics:

1. Plants of the new *Verbena* are more outwardly spreading than plants of the female parent selection.
2. Plants of the new *Verbena* are more vigorous than plants of the female parent selection.
3. Plants of the new *Verbena* and the female parent selection differ in flower color as plants of the female parent selection have pink-colored flowers.
4. Plants of the new *Verbena* are tolerant to Powdery Mildew whereas plants of the female parent selection are susceptible to Powdery Mildew.

Plants of the new *Verbena* can be compared to plants of the male parent selection. Plants of the new *Verbena* differ from plants of the male parent selection in the following characteristics:

1. Plants of the new *Verbena* flower earlier than plants of the male parent selection.
2. Plants of the new *Verbena* and the male parent selection differ in flower color as plants of the male parent selection have reddish pink-colored flowers.

Plants of the new *Verbena* can be compared to plants of the *Verbena* cultivar Sunvp-su, disclosed in U.S. Plant Pat. No. 10,311. In side-by-side comparisons conducted in Bonsall, Calif., plants of the new *Verbena* differed from plants of the cultivar Sunvp-su in the following characteristics:

1. Plants of the new *Verbena* were more upright than and not as creeping as plants of the cultivar Sunvp-su.
2. Plants of the new *Verbena* were more compact than plants of the cultivar Sunvp-su.
3. Plants of the new *Verbena* were more freely and earlier flowering than plants of the cultivar Sunvp-su.
4. Plants of the new *Verbena* and the cultivar Sunvp-su differed in flower color as plants of the cultivar Sunvp-su had red-colored flowers.

Plants of the new *Verbena* can be compared to plants of the *Verbena* cultivar Scarlena, disclosed in U.S. Plant Pat. No. 12,578. In side-by-side comparisons conducted in Bonsall, Calif., plants of the new *Verbena* differed from plants of the cultivar Scarlena in the following characteristics:

1. Plants of the new *Verbena* and the cultivar Scarlena differed in flower color as plants of the cultivar Scarlena had scarlet red-colored flowers.
2. Plants of the new *Verbena* were tolerant to Powdery Mildew whereas plants of the cultivar Scarlena were susceptible to Powdery Mildew.

BRIEF DESCRIPTION OF THE PHOTOGRAPHS

The accompanying colored photographs illustrate the overall appearance of the new *Verbena,* showing the colors as true as it is reasonably possible to obtain in colored reproductions of this type. Colors in the photographs may differ slightly from the color values cited in the detailed botanical description which accurately describe the colors of the new *Verbena.*

The photograph at the bottom the sheet comprises a side perspective view of a typical flowering plant of 'USBENA6201' grown in a container.

The photograph at the top of the sheet is a close-up view of a typical inflorescence of 'USBENA6201'.

DETAILED BOTANICAL DESCRIPTION

The aforementioned photographs and following observations and measurements describe plants grown in Bonsall, Calif., under commercial practice during the summer in an outdoor nursery with day temperatures ranging from 18° C. to 32° C. and night temperatures ranging from 13° C. to 21° C. Plants were grown with the one rooted cutting per 15-cm container for about seven weeks. In the following description, color references are made to The Royal Horticultural Society Colour Chart, 1995 Edition, except where general terms of ordinary dictionary significance are used.

Botanical classification: *Verbena hybrida* cultivar USBENA6201.

Parentage:

*Female, or seed, parent.*—Proprietary seedling selection of *Verbena hybrida* identified as code number VJL50-2, not patented.

*Male, or pollen, parent.*—Proprietary seedling selection of *Verbena hybrida* identified as code number VJL53-3, not patented.

Propagation:

*Type.*—By terminal cuttings.

*Time to initiate roots.*—About one week at 18° C.

*Time to produce a rooted young plant.*—About three weeks at 18° C.

*Root description.*—Fibrous; white in color.

*Rooting habit.*—Freely branching.

Plant description:

*Plant habit.*—Initially upright, then low to outwardly spreading and mounding; relatively compact growth habit. Freely branching habit with about ten primary lateral branches per plant each with numerous secondary branches; pinching enhances lateral branch development; dense and bushy plant habit. Vigorous growth habit.

*Plant height.*—About 18 cm.

*Plant diameter.*—About 57 cm.

Lateral branch description:

*Length.*—About 32 cm.

*Diameter.*—About 2.5 mm.

*Internode length.*—About 2.7 cm to 3 cm.

*Strength.*—Strong.

*Texture.*—Pubescent.

*Color.*—146B.

Foliage description:

*Arrangement.*—Opposite, simple.

*Length.*—About 3 cm.

*Width.*—About 1.9 cm.

*Shape.*—Narrowly deltoid.

*Apex.*—Broadly acute.

*Base.*—Acute to truncate.

*Margin.*—Crenate.

*Texture, upper and lower surfaces.*—Coarse, rough; pubescent.

*Venation pattern.*—Pinnate; arcuate.

*Color.*—Developing foliage, upper surface: 137A. Developing foliage, lower surface: 137C. Fully expanded foliage, upper surface: 147A; venation, 147B. Fully expanded foliage, lower surface: 137B; venation, 147C.

*Petiole.*—Length: About 5 mm. Diameter: About 2 mm. Texture, upper and lower surfaces: Pubescent. Color, upper and lower surfaces: 148C.

Flower description:

*Flower arrangement and habit.*—Salverform flowers arranged in hemispherical terminal racemes; flowers face upward or outward. Freely flowering habit with about 20 flowers per inflorescence.

*Natural flowering season.*—Plants flower continuously from April through October in Southern California.

*Flower longevity.*—Flowers last about one week on the plant. Flowers not persistent.

*Fragrance.*—None detected.

*Inflorescence height.*—About 4.5 cm to 5 cm.

*Inflorescence diameter.*—About 5 cm.

*Flowers.*—Appearance: Flared trumpet, corolla fused, five-parted. Diameter: About 1.7 cm. Depth (height): About 2.6 cm.

*Flower buds.*—Length: About 2.4 cm. Diameter: About 4 mm. Shape: Elongate, oblong. Color: 67B.

*Corolla.*—Arrangement: Single whorl of five fused petals. Petal lobe length: About 7 mm. Petal lobe width: About 8 mm. Petal lobe shape: Roughly cordate. Petal lobe apex: Emarginate to cordate. Petal margin: Entire. Petal texture, upper and lower surfaces: Smooth, glabrous. Color: Petal, when opening, upper surface: 61B. Petal, when opening, lower surface: 63A. Petal, fully opened, upper surface: 63A; color becoming closer to 61B with development. Petal, fully opened, lower surface: 63C to 63D. Throat: 157A. Tube: 145C to 145D.

*Calyx.*—Arrangement: One single narrow calyx tube per flower with five fused sepals. Sepal length:

About 1.6 cm. Sepal width: About 1 mm. Sepal shape: Narrowly lanceolate. Sepal apex: Acute. Sepal margin: Entire. Sepal texture, upper surface: Smooth, glabrous. Sepal texture, lower surface: Pubescent. Sepal color, upper surface: 143B. Sepal color, lower surface: 143A.

*Peduncles.*—Length: About 5.8 cm. Diameter: About 1 mm. Strength: Strong. Texture: Pubescent. Color: 144A.

*Pedicels.*—Flowers are sessile.

*Reproductive organs.*—Stamens: Quantity/arrangement: Four per flower, adnate to corolla tube. Filament length: Less than 1 mm. Filament color: 145D. Anther shape: Oval. Anther length: Less than 1 mm. Anther color: 145B. Pollen amount: Scarce. Pollen color: 1C. Pistils: Quantity: One per flower. Pistil length: About 2.2 cm. Stigma shape: Rounded. Stigma color: 144A. Style length: About 2.1 cm. Style color: 144C to 144D. Ovary color: 145A. Fruits/seed: Fruit and seed development have not been observed.

Temperature tolerance: Plants of the new *Verbena* have been observed to tolerate temperatures from about 2° C. to about 35° C.

Pathogen/pest resistance: Plants of the new *Verbena* have been observed to be tolerant to Powdery Mildew. Plants of the new *Verbena* have not been observed to be resistant to pests and other pathogens common to *Verbenas*.

It is claimed:

1. A new and distinct *Verbena* plant named 'USBENA6201' as illustrated and described.

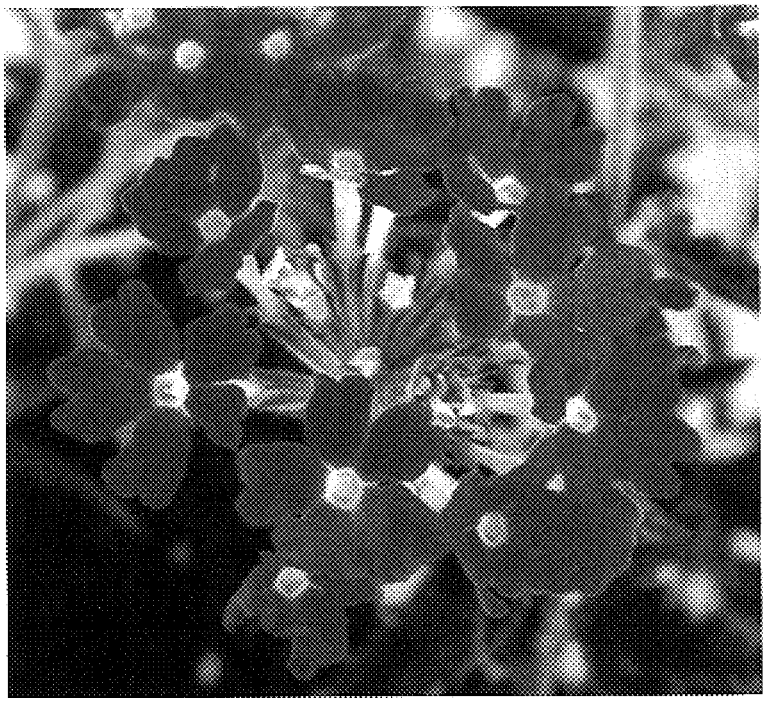
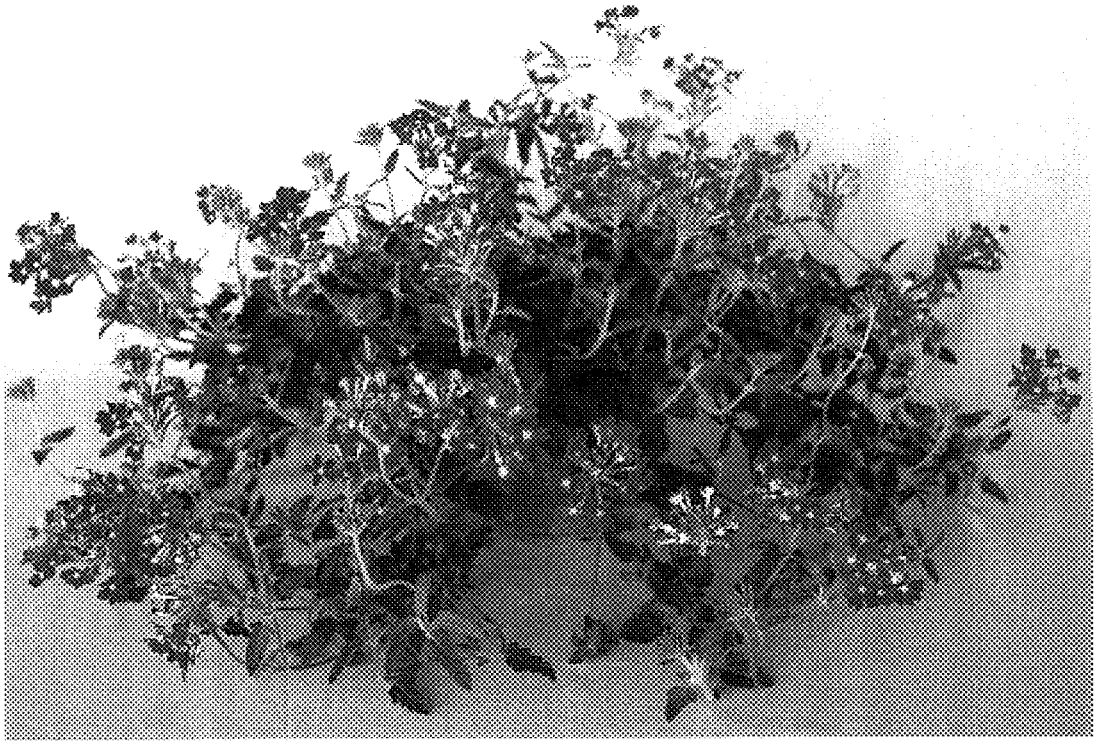

* * * * *